(12) United States Patent
Bell

(10) Patent No.: US 8,137,153 B2
(45) Date of Patent: Mar. 20, 2012

(54) BREAST PUMP SUPPORT

(76) Inventor: Wendy Corinne Bell, Coquitlam (CA)

( * ) Notice: Subject to any disclaimer, the term of this patent is extended or adjusted under 35 U.S.C. 154(b) by 150 days.

(21) Appl. No.: 12/687,024

(22) Filed: Jan. 13, 2010

(65) Prior Publication Data

US 2010/0185144 A1 Jul. 22, 2010

Related U.S. Application Data

(60) Provisional application No. 61/223,300, filed on Jul. 6, 2009.

(30) Foreign Application Priority Data

Jan. 22, 2009 (CA) ..................................... 2650723

(51) Int. Cl.
*A41C 3/00* (2006.01)
(52) U.S. Cl. ........................................... 450/36; 604/74
(58) Field of Classification Search ................... 604/74; 450/79, 82, 85, 65, 66, 75–77, 30–34, 36, 450/37, 54–58; 33/169 R, 170, 171, 173, 33/172 E
See application file for complete search history.

(56) References Cited

U.S. PATENT DOCUMENTS

| | | |
|---|---|---|
| 513,086 A | 1/1894 | Chambers |
| 949,414 A | 2/1910 | Cunningham |
| 1,167,741 A | 1/1916 | Clarke |
| 1,189,589 A | 7/1916 | Lawrence |
| 1,431,206 A | 10/1922 | Yurka |
| 1,664,214 A | 3/1928 | Hudson |
| 2,298,361 A | 10/1942 | Freund |
| 2,352,866 A | 7/1944 | Stacy |
| 2,440,466 A | 4/1948 | Freedman |
| 2,452,345 A | 10/1948 | Anselmo |
| 2,454,152 A | 11/1948 | Glick |
| 2,454,153 A | 11/1948 | Glick |
| 2,458,696 A | 1/1949 | Elias |
| 2,502,524 A | 4/1950 | Keller |
| 2,585,338 A | 2/1952 | Meares |
| 2,613,355 A | 10/1952 | Coleman |
| 2,666,919 A | 1/1954 | Spangard |
| 3,203,424 A | 8/1965 | Garutso |
| 3,425,420 A | 2/1969 | Steinberger |
| 3,459,191 A | 8/1969 | Barg |
| 3,513,852 A | 5/1970 | Seidl |
| 3,532,096 A | 10/1970 | Seidl |

(Continued)

FOREIGN PATENT DOCUMENTS

GB 440502 1/1936

(Continued)

*Primary Examiner* — Gloria Hale
(74) *Attorney, Agent, or Firm* — Christensen O'Connor Johnson Kindness PLLC

(57) ABSTRACT

The present disclosure provides a breast pump support for securing first and second milk intake components of a breast pump to the nipples of a user's breasts. The breast pump support includes an elongated band securable around the user's chest. The elongated band is defined by at least first and second opposing pieces of folded over elastic material having first and second elongated folded edges. The first and second elongated folded edges are secured to one another along their length except for along first and second sections defining first and second openings in the elongated band. The breast pump support may further include first and second means for reinforcing the elongated band adjacent to the first and second openings.

14 Claims, 5 Drawing Sheets

U.S. PATENT DOCUMENTS

| | | | | |
|---|---|---|---|---|
| 3,710,800 | A | 1/1973 | Carey | |
| 3,772,899 | A * | 11/1973 | Novi | 66/176 |
| 3,773,052 | A | 11/1973 | Belardinelli | |
| 3,785,369 | A | 1/1974 | Tallent | |
| 3,840,012 | A | 10/1974 | Rushton, Jr. | |
| 4,222,387 | A | 9/1980 | Tetu | |
| 4,270,538 | A | 6/1981 | Murphy | |
| 4,423,734 | A | 1/1984 | Schawel | |
| 4,667,345 | A * | 5/1987 | Jachowski | 2/91 |
| 4,878,879 | A | 11/1989 | Kunstadter | |
| 5,024,628 | A | 6/1991 | Sanchez | |
| 5,032,103 | A | 7/1991 | Larsson | |
| 5,050,595 | A | 9/1991 | Krafft | |
| 5,060,648 | A | 10/1991 | Zarkesh | |
| 5,094,647 | A | 3/1992 | Courtney | |
| 5,221,227 | A | 6/1993 | Michels | |
| 5,235,974 | A | 8/1993 | Miller | |
| 5,514,166 | A | 5/1996 | Silver | |
| 5,571,084 | A | 11/1996 | Palmer | |
| 5,611,086 | A | 3/1997 | Eggen | |
| 5,616,125 | A | 4/1997 | Jelks | |
| 5,624,296 | A | 4/1997 | Weber-Unger | |
| 5,679,052 | A | 10/1997 | Rucki | |
| 5,810,772 | A | 9/1998 | Niederberger | |
| 6,004,186 | A | 12/1999 | Penny | |
| 6,178,784 | B1 * | 1/2001 | Marley, Jr. | 66/173 |
| 6,192,717 | B1 * | 2/2001 | Rabinowicz | 66/177 |
| 6,213,840 | B1 | 4/2001 | Han | |
| 6,227,936 | B1 | 5/2001 | Mendoza | |
| 6,866,558 | B2 | 3/2005 | Luciano | |
| 6,887,217 | B1 | 5/2005 | Logan | |
| 6,974,361 | B2 | 12/2005 | Cravaack | |
| 7,028,509 | B2 * | 4/2006 | Mitchell et al. | 66/176 |
| 7,051,557 | B2 * | 5/2006 | Mitchell et al. | 66/179 |
| 7,094,217 | B2 | 8/2006 | Fialkoff | |
| 7,654,115 | B2 * | 2/2010 | Duckham et al. | 66/176 |
| 7,662,019 | B2 * | 2/2010 | Faircloth et al. | 450/92 |
| 2003/0191427 | A1 | 10/2003 | Jay | |
| 2007/0161330 | A1 | 7/2007 | Whitehead | |
| 2008/0039781 | A1 | 2/2008 | Bjorge | |

FOREIGN PATENT DOCUMENTS

| | | |
|---|---|---|
| GB | 723098 | 2/1955 |
| WO | 96/22116 A1 | 7/1996 |

\* cited by examiner

BREAST PUMP SUPPORT

CROSS-REFERENCE TO RELATED APPLICATION

This application claims the benefit of U.S. Provisional Patent Application No. 61/223,300, filed on Jul. 6, 2009, the disclosure of which is hereby expressly incorporated herein by reference.

BACKGROUND

It is believed by many nutritionists that breastfeeding is generally the best source of food and nutrition for an infant. Many experts and mothers believe that numerous immunological and nutritional advantages are provided by breast milk. Because of the benefits of breastfeeding, numerous breast pump devices have been developed which extract milk from a mother's breast for subsequent use when it is inconvenient for the mother to breastfeed the infant.

Although milk obtained by breast pump devices enables an infant to be conveniently fed at a later time, the act of using a breast pump to obtain the milk from the mother may cause the mother to be inconvenienced. Typically, it takes a mother approximately 10-20 minutes to obtain 2-6 ounces of milk to be used for feeding the infant. Because many mothers are "working moms," these mothers typically have many tasks to complete at home, including feeding their infants in a short period of time. Due to the limited time that a mother has to complete daily obligations, taking time out to breast-feed during busy periods of the day can cause an additional inconvenience to the mother.

While breast pump devices enable a mother to conveniently provide breast milk to the infant without having to actually nurse the infant, breast pump devices require a mother to stop or delay a task at hand to spend time pumping her breast for milk. The mother must generally sit and hold the breast pump to her breast for the amount of time that is required to extract the milk. Taking time out to sit or otherwise use her hands to hold the breast pump is inconvenient for a busy mother and usually requires the mother to delay accomplishing other tasks.

There are numerous devices available that allow a mother to use a breast pump hands-free while pumping. For instance, some brassieres include openings adapted to receive a portion of the pump therein to secure the pump against the breast while pumping. However, this type of brassiere cannot be used during regular nursing, and therefore, it causes inconvenience to the mother when switching between nursing and pumping. Other brassieres include multiple layers that allow a mother to switch between nursing and pumping; however, they often look bulky and unsightly beneath clothing. Another type of brassiere made for nursing include elastics that need to be secured around the pump. This type of brassiere assembly is difficult to use and time-consuming to assemble.

Thus, there is a need in the art to provide a breast pump system that enables a mother to conveniently collect milk without substantially encumbering or delaying the mother.

SUMMARY

The present disclosure provides a breast pump support for securing first and second milk intake components of a breast pump to the nipples of a user's breasts. The breast pump support includes an elongated band securable around the user's chest. The elongated band is defined by at least first and second opposing pieces of folded over elastic material having first and second elongated folded edges. The first and second elongated folded edges are secured to one another along their length except for along first and second sections defining first and second openings in the elongated band. The breast pump support may further include first and second means for reinforcing the elongated band adjacent to the first and second openings.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the present disclosure will become more readily appreciated by reference to the following detailed description, when taken in conjunction with the accompanying drawings, wherein.

DETAILED DESCRIPTION

Figure 1:
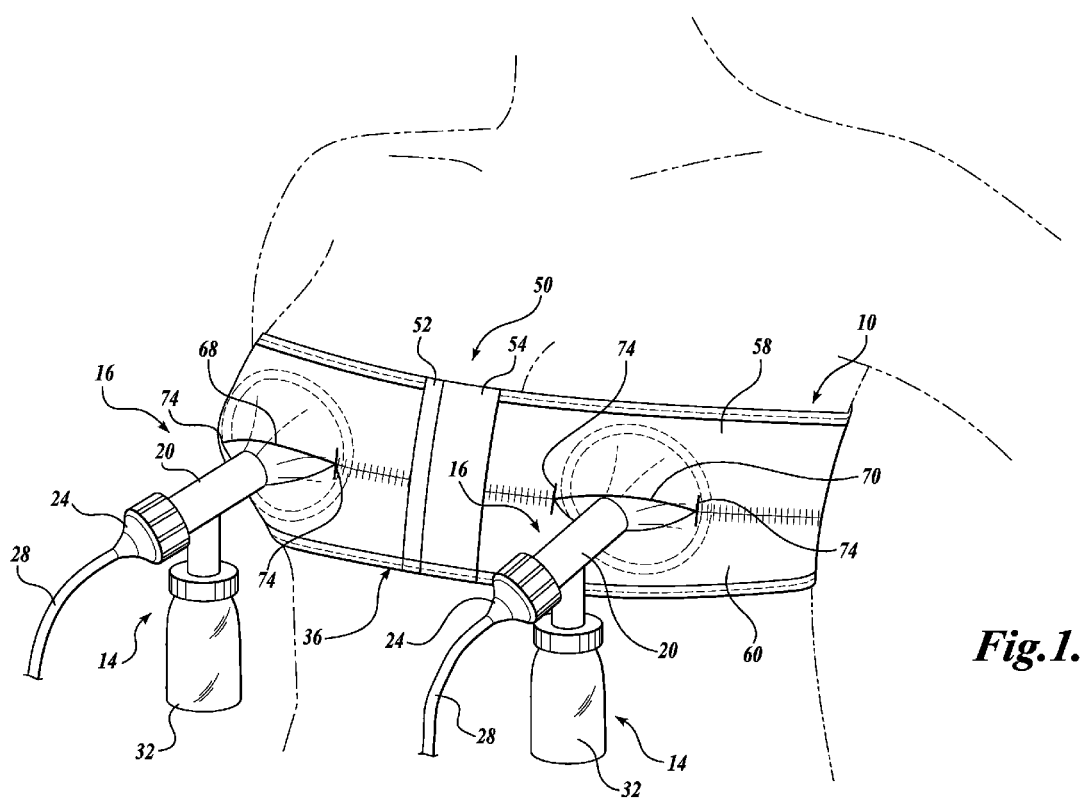
FIG. 1 is an environmental isometric view of a breast pump support constructed in accordance with one embodiment of the present disclosure, wherein the breast pump support is shown securing a portion of a breast pump to a user's body.
Figure 2:
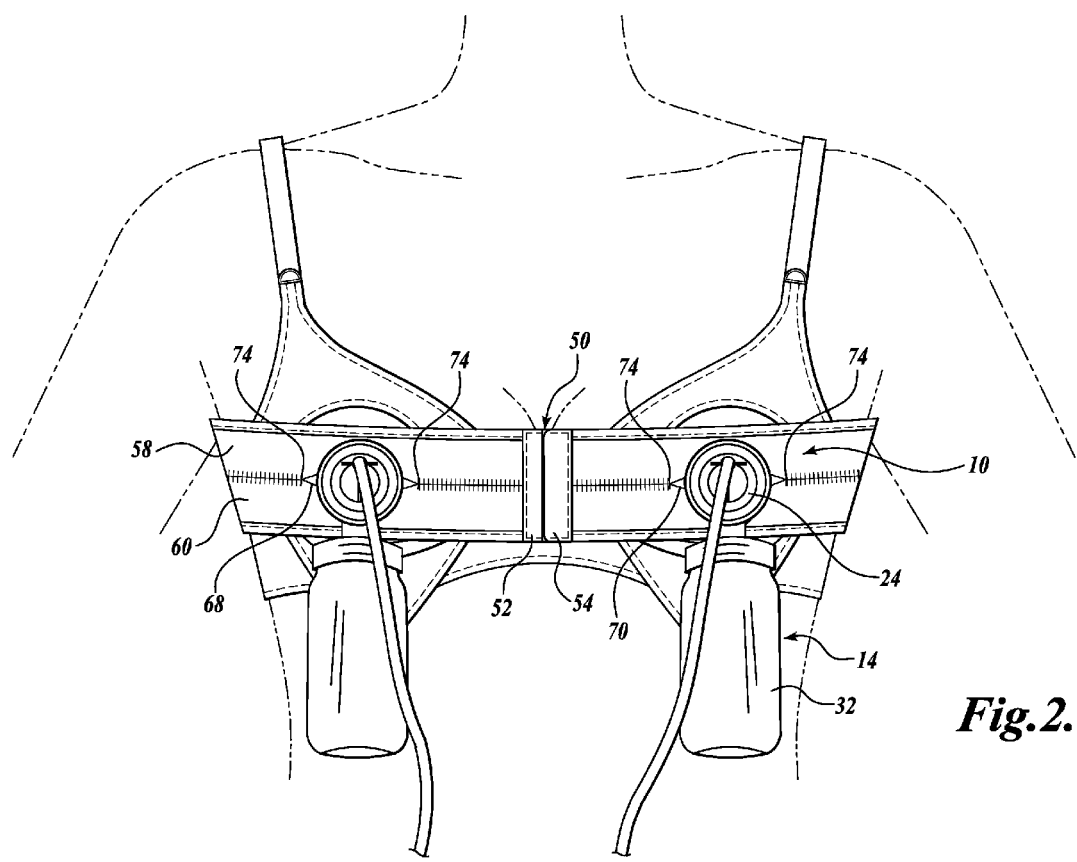
FIG. 2 is an environmental front plan view of the breast pump support of FIG. 1, wherein the breast pump support is shown securing a portion of a breast pump to a user's body over a nursing brassiere.

A breast pump support 10 constructed in accordance with one embodiment of the present disclosure is shown in FIGS. 1-6. Referring specifically to FIGS. 1 and 2, the breast pump support 10 is shown in use with a breast pump 14. Although the breast pump support 10 may be used with any suitable breast pump, the breast pump support 10 will be hereinafter described with reference to a breast pump 14 having a milk intake component or a breast shield 16 having a funnel portion 18 and a transport portion 20. The breast pump 14 further includes a pump connector 24 connected to the transport portion 20, wherein the pump connector 24 is further in communication with a pump tube 28, as is well known in the art. A milk container 32 is connected to the transport portion 20 for collecting breast milk while pumping. It should be appreciated that the breast pump support 10 may be used with any other suitable manual or automatic breast pump device; and therefore, the description herein shall not be construed as limiting the scope of the claimed subject matter.

Figure 3:
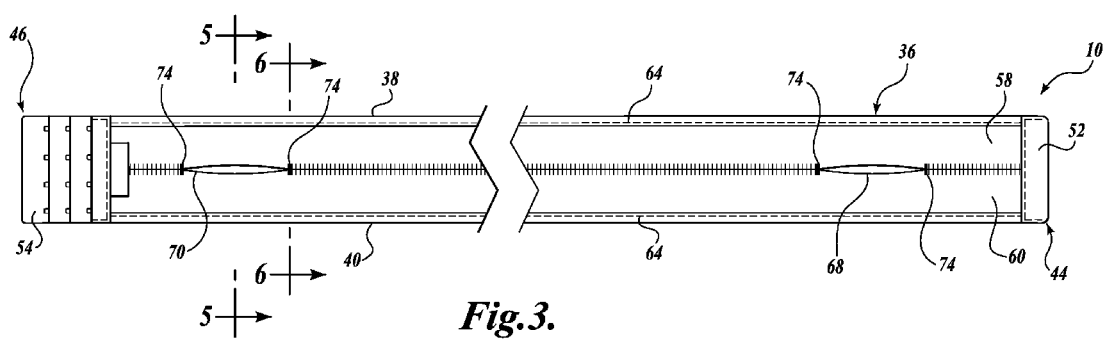
FIG. 3 is a front view of the breast pump support of FIG. 1, shown unassembled.
Figure 4:
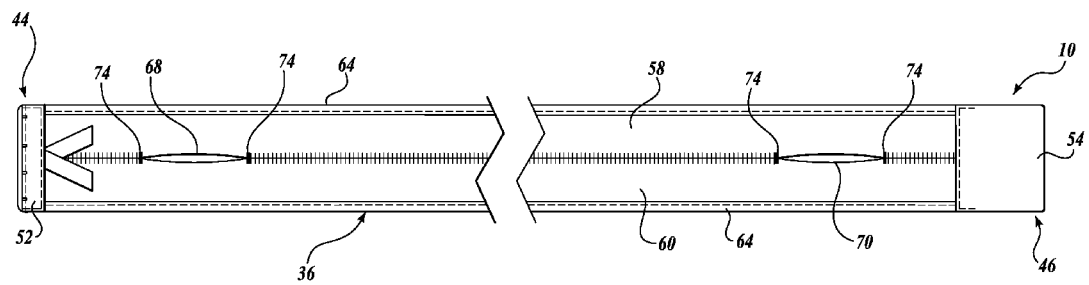
FIG. 4 is a rear view of the breast pump support of FIG. 1, shown unassembled.
Figure 5:
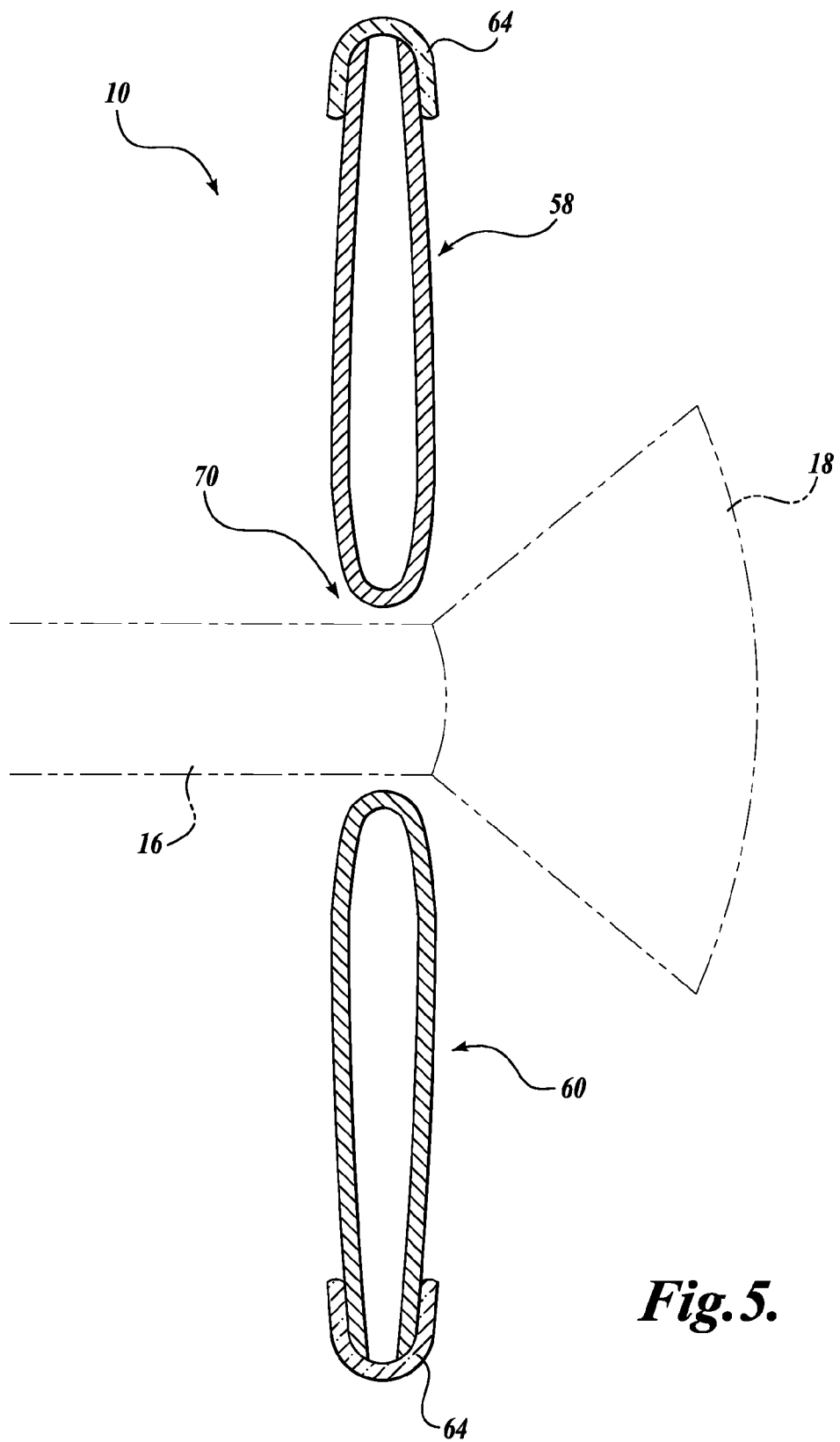
FIG. 5 is a cross-sectional view of the breast pump support of FIG. 3 taken substantially across line 5-5.
Figure 6:
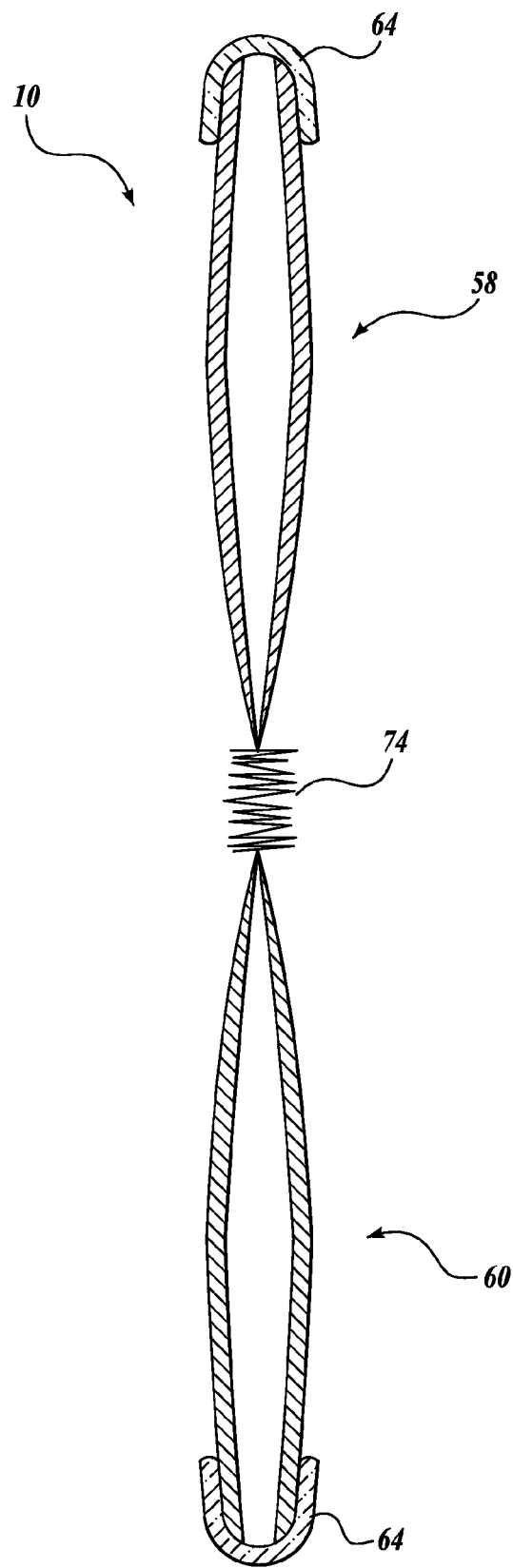
FIG. 6 is a cross-sectional view of the breast pump support of FIG. 3 taken substantially across line 6-6.

Referring to FIGS. 3 and 4, the breast pump support 10 will now be described in detail. The breast pump support 10 includes an elongated band 36 defining an upper edge 38 and a lower edge 40 that are substantially parallel to one another and define a width therebetween. Although the elongated band 36 need not necessarily be wide enough to cover the user's breasts when secured around the user's chest, the elongated band 36 is preferably sufficiently wide to cover the funnel portion 18 of the breast shield 16 when the funnel portion is secured against a user's breast. In this manner, the elongated band 36 has a sufficiently large surface area to apply pressure against the breast shield 16 and secure it against the user's breasts when pumping. However, it should be appreciated that the elongated band 36 may instead be any suitable shape and size that sufficiently secures the breast shields 16 against the user's breasts when pumping.

The elongated band 36 is also of a predetermined length to define first and second ends 44 and 46 that are attachable together to secure the elongated band 36 around the chest of a user. The elongated band 36 is of a suitable length such that it may be secured around the chest of a user in a substantially tight manner, similar to a strapless brassiere. The first and second ends 44 and 46 preferably include a suitable closure assembly to detachably secure the ends together such that the elongated band 36 may be easily secured to and removed from the user's chest. It is preferred, but not essential, that the elongated band 36 be designed such that the first and second ends 44 and 46 are secured together in substantially the center of the user's chest to allow for easy attachment and removal of the elongated band 36.

Any suitable closure assembly may be used to detachably secure the first and second ends 44 and 46 together, such as a Velcro® assembly, a zipper assembly, a button assembly, a snap assembly, etc. The elongated band 36 is shown with an adjustable hook and eye assembly 50 defined by a hook portion 52 secured to the first end 44 and an eye portion 54 secured to the second end 46. The hook portion 52 and eye portion 54 may be of any suitable design and may be secured to the first and second ends 44 and 46 in a manner well known in the art. Instead of detachably securing the ends together, it should be appreciated that the ends 44 and 46 of the elongated band 36 may instead be permanently secured together to define a bandeau that stretches to tightly fit over the user's chest.

The elongated band 36 is constructed from first and second opposing pieces of folded over material 58 and 60 preferably made from a stretchable fabric, such as a polyester and spandex blend. It should be appreciated that the pieces of material 58 and 60 may be made from any suitable fabric or other material that is at least somewhat stretchable or elastic. Each piece of material 58 and 60 is folded substantially in half along its length and stitched together or otherwise secured together in any suitable manner along its elongated open ends to define the upper and lower edges 38 and 40 of the elongated band 36. For instance, the pieces of material 58 and 60 may be secured together along their elongated open ends with binding 64, as is well known in the art. In the alternative, the first and second opposing pieces of folded over material may instead be formed from a seamless tube of material or from another suitable method that defines a folded over edge.

Referring to FIGS. 3-6, the first and second pieces of folded over material 58 and 60 are stitched together or otherwise secured together along the length of their folded elongated ends except for along two sections of the first and second pieces 58 and 60 to define first and second stitchless horizontal openings or slits 68 and 70. The stitchless horizontal slits 68 and 70 are stretchable to receive various-sized and shaped funnel portions 18 of a breast shield 16 an indefinite number of times. More specifically, without having any reinforced stitching or material secured to and surrounding the horizontal slits 68 and 70 defined by the folded over pieces of material 58 and 60, the slits 68 and 70 can be stretched significantly to allow a funnel portion 18 to pass through the opening. Moreover, the double layer construction of the horizontal slits 68 and 70 defined by the folded over pieces of material 58 and 60 increases the durability of the slits 68 and 70 and helps retain the inherent stretch in the material.

In comparison, if a hole was merely cut into the elongated band 36 to define an opening for receiving the funnel portion 18, the cut edge of material defining the hole would need to be reinforced with binding, stitching, etc., to prevent the exposed, cut edge from fraying, distorting, or otherwise weakening when stretched to receive the funnel portion 18. Since the thread, glue, etc., that would be used to reinforce the edge or otherwise secure reinforcing material to the edge is not stretchable, such reinforcement would decrease the elasticity of the opening, thereby causing the reinforcement to tear or weaken when stretched to receive the funnel portion 18. Moreover, the openings would not be capable of sufficiently stretching to accept larger or odd-sized funnel portions. Thus, using a reinforcing material around the opening decreases the durability and versatility of the support. With the horizontal slits 68 and 70 instead being defined by folded edges of material, the horizontal slits 68 and 70 can be stretched and re-stretched an indefinite number of times without distorting or otherwise weakening the material defining the horizontal slits 68 and 70.

Although the openings in the elongated band 36 are defined as horizontal slits, it should be appreciated that the elongated band 36 may instead include vertical slits or openings of any suitable shape that are made in a similar manner without departing the scope of the present disclosure. For instance, the elongated band 36 may instead be defined by more than two pieces of folded over material to define vertical slits or slits or openings of other shapes. Thus, the description herein of horizontal slits should not be seen as limiting the scope of the claimed subject matter.

The stitched edges of the elongated band 36 adjacent to the horizontal slits 68 and 70 define points of concentrated strain when the horizontal slits 68 and 70 are stretched open to receive a funnel portion 18. To prevent the two pieces of folded over material 58 and 60 from further separating, the stitched edges adjacent to the horizontal slits 68 and 70 are reinforced with any suitable means, such as bar tacks 74, or a close series of stitches transversely crossing the first and second pieces of folded over material 58 and 60. The bar tacks 74 reinforce the elongated band 36 at the points of concentrated strain when the slits 68 and 70 are stretched open to help prevent the pieces of folded over material 58 and 60 from further separating. It should be appreciated that any other suitable reinforcing means may instead be used.

With the horizontal slits 68 and 70 formed in the manner described above, the slits 68 and 70 may be stretched open to receive the funnel portion 18 of the breast shield 16 when the elongated band 36 is secured around the user's chest. Thus, to use the breast pump support 10, the elongated band 36 is first wrapped around the user's chest such that the first and second horizontal slits 68 and 70 are generally positioned to correspond to the location of the user's nipples. The first and second ends 44 and 46 are thereafter secured together through the hook and eye assembly 50, as shown in FIGS. 1 and 2. The user can adjust the tightness of the elongated band 36 around her chest through the adjustable hook and eye assembly 50. It is preferred that the elongated band 36 be tightly secured around the user's chest such that the elongated band 36 sufficiently holds the breast shield 16 against the user's chest when pumping.

After securing the elongated band 36 around the user's chest, the horizontal slits 68 and 70 are stretched open to receive the funnel portion 18 of each breast shield 16. It should be appreciated that the funnel portions 18 may be passed through the slits 68 and 70 either before or after the breast shield 16 is coupled to the pump connector 24 and/or the milk container 32. The funnel portions 18 are passed through the slits 68 and 70 such that the transport portion 20 protrudes outwardly from the user's chest. After passing the funnel portions 18 through the horizontal slits 68 and 70, the funnel portions 18 are positioned against the user's nipples and the horizontal slits 68 and 70 are released to allow the elongated band 36 to return to its unstretched position. The tautness of the elongated band 36 against the user's body secures the breast shields 16 in their position on the woman's breasts. As such, the breast pump support 10 enables the woman to pump breast milk without having to hold the breast shields 16 of the breast pump 14 against her breasts.

The breast pump support 10 may be worn over a standard nursing bra, as shown in FIG. 2. In the alternative, the breast pump support 10 may be worn over any suitable nursing garment, such as a tank top or a camisole. In this manner, the woman does not have to change between the nursing garment and the breast pump support 10 when alternating between nursing a child and pumping breast milk. In the alternative, the breast pump support 10 may be worn separate and independent of a nursing bra or any other type of support device, as shown in FIG. 1.

While the preferred embodiment of the invention has been illustrated and described, it will be appreciated that various changes can be made therein without departing from the spirit and scope of the present disclosure.

The embodiments of the present disclosure in which an exclusive property or privilege is claimed are defined as follows:

1. A breast pump support for securing at least one milk intake component of a breast pump to the nipples of a user's breasts, the breast pump support comprising an elongated band securable around a user's chest, the elongated band having a length and defined by at least a first piece of elongated fabric section that has been folded in half to form a first elongated folded edge and a first elongated open edge and a second piece of elongated fabric section that has been folded in half to form a second elongated folded edge and a second elongated open edge, the first and second elongated folded edges aligned adjacent to each other and secured to one another along their length except for along at least a first section of the first and second elongated folded edges defining a first opening between the first and second elongated folded edges in the elongated band.

2. The breast pump support of claim 1, further comprising means for reinforcing the elongated band adjacent to the first opening.

3. The breast pump support of claim 2, wherein the means for reinforcing the elongated band comprises bar tacks.

4. The breast pump support of claim 1, wherein the first and second elongated open edges define upper and lower edges of the elongated band.

5. The breast pump support of claim 4, wherein the first elongated open edge is secured along its length and the second elongated open edge is secured along its length.

6. The breast pump support of claim 1, wherein the first and second pieces of elongated fabric sections are elastic.

7. The breast pump support of claim 1, wherein the elongated band includes first and second ends that are detachably securable to one another.

8. The breast pump support of claim 7, wherein the first and second ends of the elongated band are detachably securable to one another through an adjustable closure assembly.

9. The breast pump support of claim 1, wherein the first and second pieces of elongated fabric sections are stretchable such that the first opening can receive breast milk intake components of various shapes and sizes.

10. The breast pump support of Claim 1 wherein the first and second elongated folded edges are aligned adjacent to each other and secured to one another along at least a portion of their length except for along at least first and second sections of the first and second elongated folded edges, wherein the second section defines a second opening between the first and second elongated folded edges in the elongated band.

11. The breast pump support of claim 10, wherein the location of the first and second openings generally correspond to the location of first and second nipples of a user's breasts.

12. A breast pump support for securing first and second milk intake components of a breast pump to the nipples of a user's breasts, the breast pump support comprising:
  (a) an elongated band securable around a user's chest, the elongated band having a length and defined by at least a first piece of elongated fabric section that has been folded in half to form a first elongated folded edge and a first elongated open edge and a second piece of elongated fabric section that has been folded in half to form a second elongated folded edge and a second elongated open edge, the first and second elongated folded edges aligned adjacent to each other and secured to one another along their length except for along at least first and second sections of the first and second elongated folded edges defining first and second openings in the elongated band between the first and second elongated folded edges; and
  (b) first and second means for reinforcing the elongated band adjacent to the first and second openings.

13. The breast pump support of claim 12, wherein the first and second means for reinforcing the elongated band comprise bar tacks.

14. The breast pump support of claim 12, wherein the first and second pieces of elongated fabric sections are stretchable such that the first and second openings can receive first and second breast milk intake components of various shapes and sizes.

* * * * *